(12) United States Patent
Lee et al.

(10) Patent No.: US 9,686,484 B2
(45) Date of Patent: Jun. 20, 2017

(54) APPARATUS FOR ACQUIRING AND PROJECTING BROADBAND IMAGE CAPABLE OF IMPLEMENTING VISIBLE LIGHT OPTICAL IMAGE AND INVISIBLE LIGHT FLUORESCENCE IMAGE TOGETHER

(71) Applicant: KOREA PHOTONICS TECHNOLOGY INSTITUTE, Gwangju (KR)

(72) Inventors: Byeong Il Lee, Gwangju (KR); In Hee Shin, Gwangju (KR); Jae Seok Park, Gimhae-si (KR); Joo Beom Eom, Gwangju (KR); Hyung Ju Park, Gwangju (KR); Seok Ki Kim, Goyang-si (KR)

(73) Assignee: KOREA PHOTONICS TECHNOLOGY INSTITUTE, Gwangju (KR)

( * ) Notice: Subject to any disclaimer, the term of this patent is extended or adjusted under 35 U.S.C. 154(b) by 0 days.

(21) Appl. No.: 14/400,356

(22) PCT Filed: Sep. 2, 2014

(86) PCT No.: PCT/KR2014/008183
§ 371 (c)(1),
(2) Date: Nov. 11, 2014

(87) PCT Pub. No.: WO2015/030562
PCT Pub. Date: Mar. 5, 2015

(65) Prior Publication Data
US 2016/0277687 A1    Sep. 22, 2016

(30) Foreign Application Priority Data

Sep. 2, 2013    (KR) .................. 10-2013-0105021

(51) Int. Cl.
*G01N 21/64*    (2006.01)
*A61B 5/00*    (2006.01)
(Continued)

(52) U.S. Cl.
CPC ........... *H04N 5/332* (2013.01); *A61B 5/0033* (2013.01); *A61B 5/0059* (2013.01);
(Continued)

(58) Field of Classification Search
None
See application file for complete search history.

(56) References Cited

U.S. PATENT DOCUMENTS

2003/0078477 A1* 4/2003 Kang ..................... A61B 1/042
 600/178
2004/0225222 A1* 11/2004 Zeng ..................... A61B 1/043
 600/476

(Continued)

*Primary Examiner* — Reza Aghevli
(74) *Attorney, Agent, or Firm* — Lex IP Meister, PLLC (57) ABSTRACT

Provided is an apparatus for acquiring and projecting a broadband image. The apparatus includes a probe unit provided with a white light source unit configured to emit white light for acquiring a visible light image to a subject, a fluorescence excitation light source unit configured to emit fluorescence excitation light for acquiring an invisible light fluorescence image, an image acquisition unit configured to receive an invisible light fluorescence image signal for the subject, and an image projection unit configured to project an image onto the subject; and an image processing unit configured to process an image received from the image acquisition unit. This apparatus may simultaneously acquire and display the visible light image and the invisible light fluorescence image.

6 Claims, 4 Drawing Sheets

(51) Int. Cl.
*H04N 5/33* (2006.01)
*H04N 5/232* (2006.01)
*H04N 9/31* (2006.01)

(52) U.S. Cl.
CPC .......... *A61B 5/0071* (2013.01); *A61B 5/7225* (2013.01); *A61B 5/7445* (2013.01); *G01N 21/6456* (2013.01); *H04N 5/23293* (2013.01); *H04N 9/3179* (2013.01); *G01N 2201/062* (2013.01); *G01N 2201/06113* (2013.01); *G01N 2201/125* (2013.01)

(56) References Cited

U.S. PATENT DOCUMENTS

| | | | |
|---|---|---|---|
| 2010/0234762 A1* | 9/2010 | Pond | G01N 33/57407 600/567 |
| 2011/0250633 A1* | 10/2011 | Jansen | G01N 1/312 435/39 |
| 2011/0275900 A1* | 11/2011 | Gilhuly | A61B 1/00142 600/162 |
| 2013/0303403 A1* | 11/2013 | Ozaki | G01N 21/6452 506/12 |
| 2014/0081095 A1* | 3/2014 | Krishnan | A61B 5/0059 600/306 |
| 2016/0022389 A1* | 1/2016 | Esbech | G01J 3/513 250/208.1 |

* cited by examiner

APPARATUS FOR ACQUIRING AND PROJECTING BROADBAND IMAGE CAPABLE OF IMPLEMENTING VISIBLE LIGHT OPTICAL IMAGE AND INVISIBLE LIGHT FLUORESCENCE IMAGE TOGETHER

TECHNICAL FIELD

The present invention relates to an apparatus for acquiring and projecting a broadband image capable of implementing a visible light optical image and an invisible light fluorescence image together, and more particularly, to an apparatus for acquiring and projecting a broadband image that implements a visible light optical image through a camera by radiating white light, implements an invisible light fluorescence image by radiating fluorescence excitation light, and also visually implements an area and shape in which fluorescence is revealed by projecting the implemented fluorescence image to a position where the fluorescence is revealed.

BACKGROUND ART

Recently, clinical research using fluorescence products has been conducted, and much research has been deployed to effectively detect and implement a fluorescence signal.

In particular, as research is widely conducted on molecular imaging, advanced research using fluorescence is in progress globally.

Korean Patent Application Nos. 10-2001-7016066, 10-2002-7012264, 10-2006-7021266, and 10-2012-7012905 disclose a variety of information associated with detection of fluorescence signals, and fluorescence products.

Fluorescence is used to configure a system with relatively simple equipment, such as an excitation light source, a band filter, and a light detector thereby allowing wide use and also having very high utility in terms of cost, compared to other detection apparatuses. In particular, when fluorescence in the visible light range of 400 to 700 nm is used, the fluorescence may be observed with the naked eye and have good skin permeability, thereby increasing medical applicability.

However, fluorescence has limitations in that its signal-to-noise ratio is lower than that of luminescence and its sensitivity is reduced due to the influence of barriers such as light scattering, autofluorescence, and the like and several factors such as a light source and a filter.

To overcome these limitations, research has been widely conducted on near infrared fluorescence products in the range of 780 to 2000 nm, which has permeability better than that of the visible light region. In addition, an inspection method that is applicable to a preclinical trial and a clinical trial is being developed because a signal for depth information may be acquired.

For a method used in a preclinical trial, research is being conducted to observe a route to a tumor and a treatment process after developing a probe that is combined with fluorescence material to perform targeting to diseases and then providing an intravenous injection.

On the other hand, evaluation of a soft tissue may be widely used to evaluate clinical characteristics. Representatively, indocyanine green (ICG), which is a near infrared fluorescence approved by the Food and Drug Administration (FDA), is used to check circulation in blood as a blood contrast medium and to locate sentinel lymph nodes (SNs) that inform a tumor metastasis degree in a breast cancer patient.

Like this, a variety of research is being conducted, such as clinical research using fluorescence products and research for effectively detecting and implementing a fluorescence signal. As a result of such research, various fluorescence imaging apparatuses are being developed. However, the apparatuses do not obtain, actually, a result that is applicable to a clinical trial.

First, at present, there is not yet developed a technology for effectively visualizing a fluorescence image in addition to implementing the fluorescence image.

In addition, there is not sufficiently developed a technology for implementing a visible light optical image on a fluorescence revelation region in addition to a fluorescence image.

A technology for acquiring and projecting fluorescence and visible light is essential to the medical field and is widely used when sentinel lymph nodes are visualized. Stable implementation of the technology is important in a surgery and clinical environment. Furthermore, use of an analog environment and a digital environment at the same time is not technically difficult. However, practically, since analog devices and digital devices should be separately installed, supplement policies are required in a site where emergencies may occur along the lines of movement of a surgery operator and an operation assistant, disconnection may occur in equipment, a surgery operator and an operation assistant may get a fall. In particular, though a computer is powered off during treatment, it is essentially needed for a minimum defense policy capable of continuous treatment in an analog environment.

Accordingly, a convergence technology is required to develop based on various image processing techniques that have been already developed. In particular, a method that is effectively applicable to a clinical trial should be proposed.

DISCLOSURE

Technical Problem

The present invention is directed to providing an apparatus for acquiring and projecting an image that may simultaneously acquire a visible light optical image and an invisible fluorescence image for the same position of a subject.

The present invention is also directed to providing an apparatus for acquiring and projecting an image that may maximize visualization of the invisible light fluorescence image by projecting the acquired invisible light fluorescence image onto a part in which a fluorescence image is generated.

The present invention is also directed to providing an apparatus for acquiring and projecting an image that may overcome a problem for an unexpected accident, such as failure in a computer, which may occur in a clinical trial using an analog camera for acquiring a fluorescence image.

The present invention is also directed to providing an apparatus for acquiring and projecting an image that may implement a color digital image obtained by visible light and an analog image and a digital image obtained by invisible light together to perform temporal comparison on the same subject in real time, thus maximizing clinical application possibility.

Technical Solution

One aspect of the present invention provides an apparatus for acquiring and projecting a broadband image, the apparatus including: a probe unit provided, on a probe housing of the probe unit, with a white light source unit configured to emit white light for acquiring a visible light image to a subject, a fluorescence excitation light source unit configured to emit fluorescence excitation light for acquiring an invisible light fluorescence image, and an image acquisition unit configured to receive an invisible light fluorescence image signal for the subject, and an image projection unit configured to project an image onto the subject; and an image processing unit configured to process an image received from the image acquisition unit.

The image acquisition unit, the image projection unit, and the white light source unit may be arrayed in a central region corresponding to a set first radius from a center of the front surface of the probe housing, and the fluorescence excitation light source unit may be arranged in a surrounding region between the central region and an edge of the probe housing that is positioned in a direction in which a radius increases from the central region.

The fluorescence excitation light source unit may include a light emitting diode that emits a first band of light, and the apparatus may further include a laser illumination light source unit positioned in a surrounding region of the probe housing, and configured to emit laser light that is within the first band and has a wavelength width less than that of the first band.

The image acquisition unit may be configured to receive both the invisible light fluorescence image signal and an image signal of a visible light that is incident from the subject, and the image processing unit may include: an image separation unit configured to separate the invisible light fluorescence image signal and the visible light image signal received from the image acquisition unit; a color digital camera configured to capture a visible image separated by the image separation unit; and an analog camera configured to capture an invisible fluorescence image separated by the image separation unit.

The image processing unit may include: a first display unit configured to display an image captured by the color digital camera; a second display unit configured to display an analog fluorescence image captured by the analog camera; an analog-to-digital converter configured to convert a signal of the analog fluorescence image captured and transmitted by the analog camera into a digital image signal; a third display unit configured to receive the digital image signal from the analog-to-digital converter and display the received digital image signal; and a digital image projector configured to receive the digital image signal from the analog-to-digital converter, convert the received digital image signal into a digital image projection signal, and transmit the converted digital image projection signal such that the converted digital image projection signal is projected through the image projection unit.

The apparatus may further include a controller configured to store a signal of a visible light image captured by the color digital camera and the digital image signal generated by the analog-to-digital converter in a database.

Advantageous Effects

As described above, according to the apparatus for acquiring and projecting a broadband image of the present invention, the visible light image and the invisible light fluorescence image may be simultaneously acquired and then displayed, and the acquired fluorescence image is projected onto a position where a fluorescence signal may be revealed, thus visually providing a position and shape in which the fluorescence signal is generated.

In addition, the fluorescence image acquired by the analog camera may be provided although a problem occurs such as an error of a digital image processing device such as a computer, thereby handing an unexpected accident during a surgery operation.

MODES OF THE INVENTION

Hereinafter, an apparatus for acquiring and projecting a broadband image according to preferred embodiments of the present invention will be described in more detail with reference to the accompanying drawings.

Figure 1:
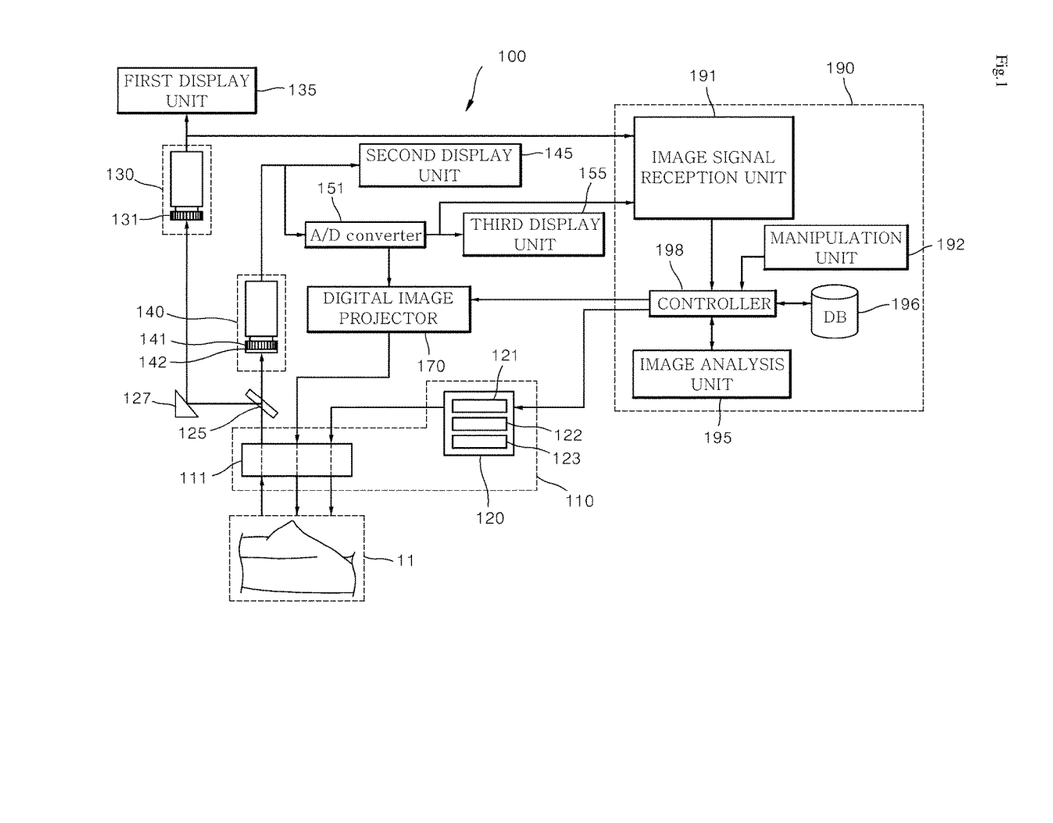
FIG. 1 is a view showing an apparatus for acquiring and projecting a broadband image according to an embodiment of the present invention.

FIG. 1 is a view showing an apparatus for acquiring and projecting a broadband image according to an embodiment of the present invention.

Referring to FIG. 1, an apparatus for acquiring and projecting a broadband image according to an embodiment of the present invention includes a probe unit 110, a light divider 120, a color digital camera 130, an analog camera 140, an analog-to-digital converter (A/D converter) 151, a digital image projector 170, and a control unit 190.

Figure 2:
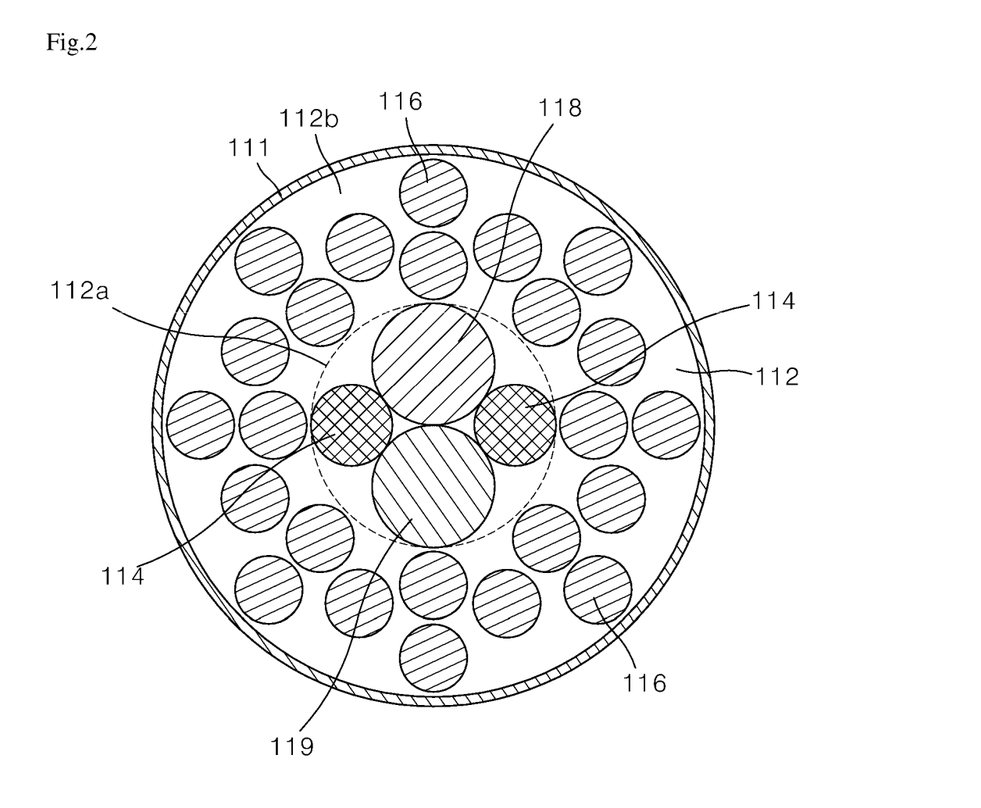
FIG. 2 is a view showing a front surface of a probe housing of an apparatus for acquiring and projecting a broadband image according to an embodiment of the present invention.

The probe unit 110 is configured to emit light to a subject 11 through a probe housing 111 and to receive light that is incident through the probe housing 111 from the subject 11, and will be described with reference to FIG. 2.

The probe unit 110 is configured to emit light to the subject 11 through a front surface 112 of the probe housing 111, receive light that is incident from the subject 11, and project an image onto the subject 11.

The probe housing 111 includes a white light source unit 114 configured to emit white light for acquiring a visible light image to the subject 11 through the front surface, a fluorescence excitation light source unit 116 configured to emit fluorescence excitation light for acquiring an invisible light fluorescence image, an image acquisition unit 118 configured to receive an invisible light fluorescence image signal for the subject 11, and an image projection unit 119 configured to project an image onto the subject 11.

The white light source unit 114 may be a light source that may emit white light.

The white light source unit 114 may include, for example, at least one of a light emitting diode, a semiconductor laser, a halogen lamp, and an incandescent lamp.

The fluorescence excitation light source unit 116 may be a light source for emitting fluorescence excitation light to acquire an invisible light fluorescence image on an inside of the subject.

The white light source unit 24 may include, for example, at least one of a light emitting diode, a semiconductor laser, a halogen lamp, and an incandescent lamp.

In this case, preferably, the fluorescence excitation light source unit 116 may emit light in the band of 700 nm to 800 nm.

Figure 3:
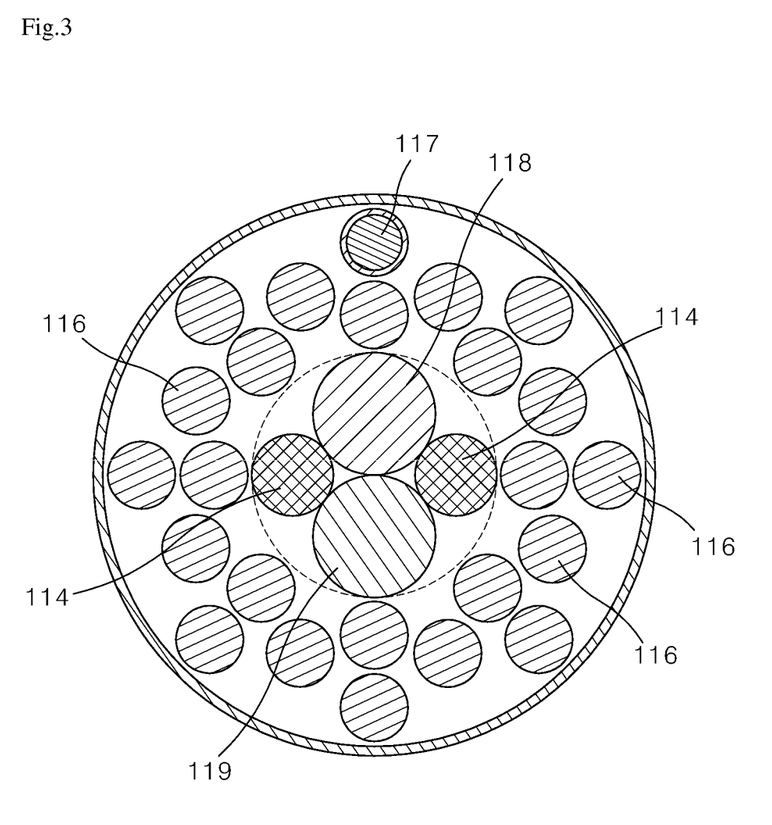
FIG. 3 is a view showing a front surface of a probe housing of an apparatus for acquiring and projecting a broadband image according to another embodiment of the present invention.

When a light emitting diode is used as the fluorescence excitation light source unit 116, as shown in FIG. 3, a surrounding region 112b is further provided with a laser illumination light source unit 117.

In this case, the fluorescence excitation light source unit 116 is a light emitting diode that emits a first band of light, and the laser illumination light source unit 117 emits laser light that is within the first band and has a wavelength width less than that of the first band.

As an example, the laser illumination light source unit 117 may emit light having a central wavelength of 780 nm, and the fluorescence excitation light emitting diode may emit a first band of light having a wavelength of 760 to 790 nm.

As such, the laser light that is applied for fluorescence excitation around a center wavelength within a band of light of a fluorescence excitation light emitting diode is radiated to the subject 11, thus increasing recognition of a fluorescence image of the subject 11.

In addition, unlike the shown example, the laser illumination light source unit 117 may be disposed at a central region 112a of the probe housing 111.

Figure 4:
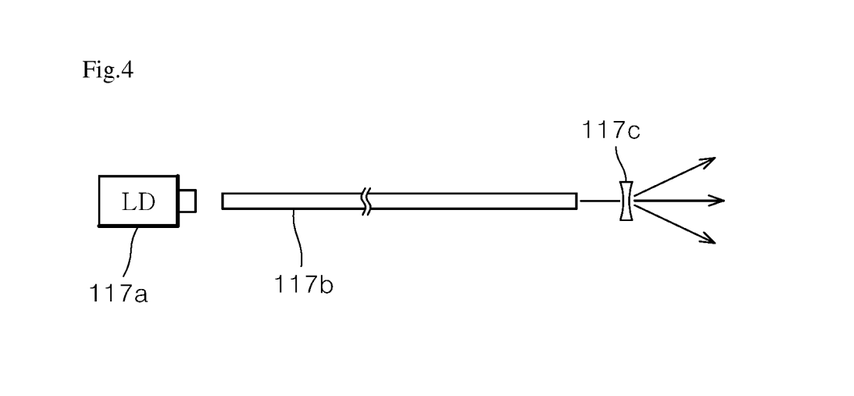
FIG. 4 is a view showing an example of an optical transmission structure of a laser illumination light source of FIG. 3.

As shown in FIG. 4, the laser illumination light source unit 117 may include a laser light source 117a, an optical waveguide 117b, and a diffusion lens 117cThe optical waveguide 117b may have a separate optical transmission space in the probe housing 111 or be an optical fiber. The diffusion lens 117c is used to diffuse the laser light radiated to the subject at a certain angle to illuminate a certain range of the subject 11 with the laser light.

When the optical fiber is used as the optical waveguide 117b, extended to the front surface of the probe housing 112, and equipped with the lens 117c at an end portion to form a desired emission angle, the size of the probe housing 111 may be reduced.

The image acquisition unit 118 may be provided in the front surface of the probe housing 111 to expose one end thereof such that an invisible light fluorescence image signal for the subject 11 may be acquired.

Preferably, the image acquisition unit 118 is configured to acquire both an invisible light fluorescence image signal and a visible light image signal for the subject 11.

Here, the invisible light fluorescence image signal refers to a signal generated by exciting fluorescence material injected into the subject using fluorescence excitation light.

The image acquisition unit 118 may be formed to have an optical path divided in the probe housing 111 to transmit light that is incident from the subject 11 to the image separation unit 125 which will be described below or formed with at least one optical fiber.

The image projection unit 119 may be provided to project an image onto the subject 11 through the front surface of the probe housing 111.

The image projection unit 119 may be formed to have an optical waveguide path divided in the probe housing 111 to transmit an image projected to the subject 11.

Here, a lens (not shown) for increasing light collection efficiency and projection efficiency may be installed in the image acquisition unit 118 and the image projection unit 119.

Preferably, the image acquisition unit 118, the image projection unit 119, and the white light source unit 114 are arrayed in a central region 112a corresponding to a set first radius from a center of the front surface 112 of the probe housing 111 formed in a circular form, and the fluorescence excitation light source unit 116 is arranged concentrically in a surrounding region 112b between the central region 112a and an edge of the probe housing 111.

Two white light source units 114 are arranged symmetrically with respect to the center of the front surface 112 of the probe housing 111, and the fluorescence excitation light source unit 116 is arranged concentrically in the front surface 112 of the probe housing 111 and thus may concentrically provide uniform light quantity distribution.

The light source driving unit 120 includes a white light source driving unit 121 for driving the white light source unit 114, a fluorescence excitation light source driving unit 122 for driving the fluorescence excitation light source unit 116, and a laser light source driving unit 123 for driving the laser illumination light source unit 117.

The light source driving unit 120 is controlled by a controller 198.

The light source driving unit 120 and the probe unit 110 may be formed as one body.

An image processing unit processes an image received from the image acquisition unit 118.

The image processing unit includes an image separation unit 125, a color digital camera 130, a first display unit 135, an analog camera 140, a second display unit 145, an analog-to-digital converter (A/D converter) 151, a third display unit 155, a digital image projector 170, and a control unit 190.

The image separation unit 125 is installed on a path of light that is received from the image acquisition unit 118 and transmitted to separate the invisible light fluorescence image signal and the visible light image signal into different paths.

The image separation unit 125 includes a dichroic mirror, which transmits or reflects light depending on wavelength.

That is, the dichroic mirror shown as the image separation unit 125 is disposed to be inclined with respect to a light incident path to reflect the visible light image signal and transmit the invisible light fluorescence image signal.

Reference number 127 indicates a path changing mirror for changing an optical path of the visible light image signal separated by the image separation unit 125 to a light incident direction of the color digital camera 130.

The color digital camera 130 captures an image of visible light that is separated by and incident from the image separation unit 125.

The color digital camera 130 converts the visible light image incident through a lens 131 into a digital image signal and outputs the converted digital image signal.

The first display unit 135 displays the digital image signal output from the color digital camera 130.

The analog camera 140 captures the invisible light fluorescence image that is incident from the image separation unit 125 and output the captured analog fluorescence image signal.

Reference number 141 indicates a lens, and reference number 142 is a band filter that passes light in a set band, for example, 800 to 850 nm.

The second display unit 145 displays the analog fluorescence image signal captured by the analog camera 140.

The analog-to-digital converter 151 converts the analog fluorescence image signal captured and transmitted by the analog camera 140 into a digital image signal.

The third display unit 155 receives the digital image signal converted by the analog-to-digital converter 151 and displays the received digital image signal.

The digital image projector 170 receives the digital image signal from the analog-to-digital converter 151, converts the received digital image signal into a digital image projection signal, and transmits the converted digital image projection signal such that the converted digital image projection signal may be projected through the image projection unit 119 of the probe housing 111.

The digital image projector 170 may be configured to receive an image obtained by performing, by an image analysis unit 195, noise removal or other correction on the digital image signal converted by the analog-to-digital converter 151.

The control unit 190 includes an image signal reception unit 191, a manipulation unit 192, an image analysis unit 195, a database 196, and a controller 198.

The image signal reception unit 191 receives a visible light image signal captured by the color digital camera 130 and a digital image signal for a fluorescence image generated by the analog-to-digital converter 151 under control of the controller 198.

The manipulation unit 192 is configured to set a function supported by the controller 198.

The image analysis unit 195 analyzes an image received from the image signal reception unit 191 or an image stored in the database 196 under control of the controller 198.

The image analysis unit 195 may be configured to perform processing such that a visible light image and a fluorescence image are positioned at the same position. In addition, the image analysis unit 195 is configured to perform a three-dimensional (3D) operation to generate a 3D image when the image analysis unit 195 is set to calculate a depth.

The controller 198 stores the image received from the image signal reception unit 191 or an image analyzed by the image analysis unit 195 in the database 196.

Preferably, when the acquired image signals are applied to a surgery operation, the controller 198 is configured to capture images before, during, and after the surgery operation to allow the images to be compared and checked, and store the images in the database 196.

In addition, the controller 198 controls driving of the color digital camera 130, the analog camera 140, and the light source driving unit 120 according to a set image acquisition and projection process.

Figure 5:
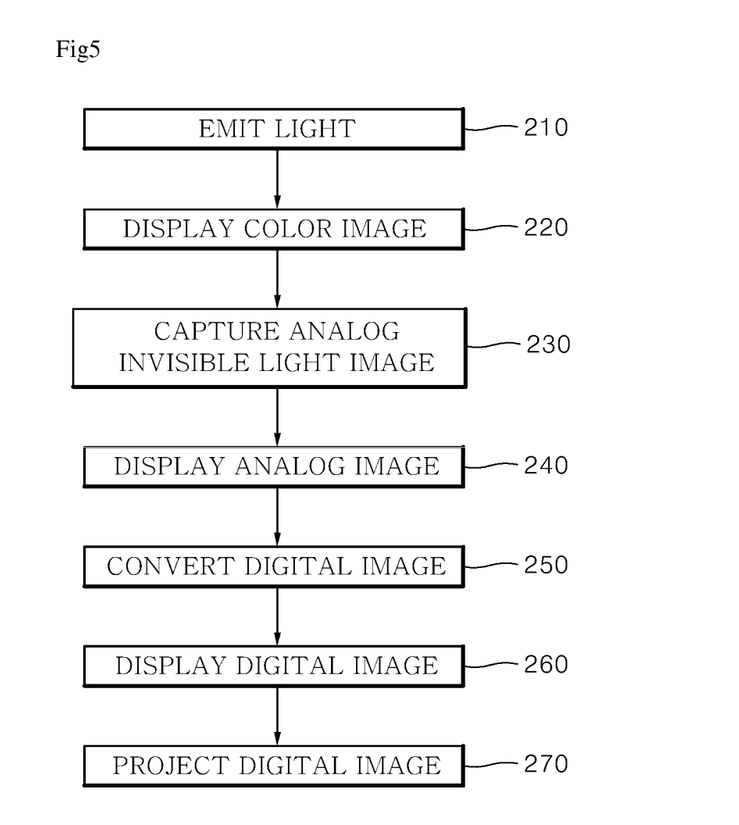
FIG. 5 is a flowchart showing an image processing process of an apparatus for acquiring and projecting a broadband image according to an embodiment of the present invention.

An image acquisition and projection process under control of the controller 198 will be described with reference to FIG. 5.

First, the process includes controlling the light source driving unit 120 to perform emitting so as to generate visible light and invisible light fluorescence through the probe housing 111 in step 210. That is, the controller 198 performs control such that the white light generation unit 114, the fluorescence excitation light source unit 116, and the laser illumination light source unit 117 emit light.

Next, the process includes displaying a visible light image on the subject 11 captured by the color digital camera 130, that is, an outer cover of the subject 11 on the first display unit 135 in step 220. In addition, the image displayed by the first display unit 135 may be stored in the database (DB) 196 under control of the controller 198.

The process includes capturing, by the analog camera 140, an analog invisible fluorescence image on the subject 11 in step 230. That is, the analog invisible fluorescence image on the fluorescence material positioned inside the subject 11 is captured by the analog camera 140.

The signal of the fluorescence image captured by the analog camera 140 is displayed as an analog image through the second display unit 145 in step 240. In this case, an image of the outer cover of the subject 11 may be viewed through the first display unit 135, and a fluorescence image on an inside of the subject 11 may be viewed together through the second display unit 145. In addition, the process includes receiving, by the analog-to-digital converter 151, an analog invisible fluorescence image signal from the analog camera 140 to convert the analog invisible fluorescence image signal into a digital image signal in step 250. The digital image signal converted in step 250 is stored in the database 196.

Further, the process includes receiving, by the third display unit 155, the digital image signal from the analog-to-digital converter 151 and displaying a digital image in step 260. In this case, the inside of the subject 11 may also be checked using the digital image.

Furthermore, the process includes projecting the digital image signal converted by the analog-to-digital converter 151 onto the subject 11 through the digital image projector 170 in step 270. Accordingly, a digital image is projected onto the outer cover of the subject through the digital image projector 170 in addition to the white light source and the laser light source, and thus a user may check an accurate potion of the outer cover where a fluorescence image is generated by the projected digital image.

When the digital image projected onto the subject 11 and the image generated by visible light illuminating the subject 11 with the white light source unit 114 are incident to the color digital camera 130 by performing step 270, a digital image projected into the subject 11 in addition to a simple image on an outer cover of the subject 11 is captured by the color digital camera 130, displayed by the first display unit 135, and stored in the database 196, and thus a user may check an accurate position of a region where a fluorescence image is generated through the first display unit 135 and may compare and analyze data whenever necessary.

As such, the user may check an outer cover of the subject 11 through the first display unit 135 that displays a color image and may view an invisible light fluorescence image on an inside of the subject 11 through the second display unit 145 as an analog image or through the third display unit 155 as a digital image. That is, the user may check one portion of the subject 11 in various methods. In addition, a surgery operator may compare the images and carry out a more accurate surgery operation. Furthermore, even when one of the first to third display units 135, 145, and 155 or members is abnormal, a surgery operator may check a normal image and maintain the surgery operation stably even in an emergency case.

According to the above-described apparatus 100 for acquiring and projecting an image, an image on an outer cover of the subject 11 may be obtained by the color digital camera 130 as a visible light image and a fluorescence image generated due to fluorescence revelation of the inside of the subject may be obtained from an invisible light fluorescence image captured by the analog camera 140. In particular, both visible light and invisible fluorescence excitation light may be provided concentrically in the probe housing 111 and radiated to the subject 11, and fluorescence images on the outer cover and the inner side of the same subject 11 may be acquired together from the radiated light, thus enabling mutual comparison between the outer cover and the inner side of the same part.

In addition, although a member for converting an analog invisible light fluorescence image signal into a digital image signal, for example, a computer or graphic card has an error, the error may not affect an image displayed by the second display unit 145 for displaying an analog image and thus may be stably used even in several problems that may occur when applying a clinical trial.

When a digital image corresponding to the acquired fluorescence image is projected by the digital image projector 170 onto an outer cover of the subject 11 through the image projection unit 119, a surgery operator may perform an operation while observing an image projected onto the outer cover of the subject 11 and accurately checking a position where a fluorescence image is actually generated in the inside with naked eyes.

Furthermore, for the image captured by the color digital camera 130, an image radiated by the image projection unit 119 in addition to an image of an outer cover of the subject 11 is captured by the color digital camera 130 and displayed by the first display unit 135. Thus a surgery operator may perform an operation while observing a screen image of the first display unit 135 and easily checking states of outer and inner sides of the subject 11.

The above-described apparatus is simply not limited to observing only a near infrared signal or a visible light signal, and thus may be used in various clinical environments by acquiring the two signals at the same time. For example, the apparatus may be variously utilized when tracking a fluorescence signal in a skin surface, tracking a lymph node under a surface layer, and surgery operations, such as a breast cancer operation, a stomach cancer operation, a malignant melanoma operation, and the like.

The invention claimed is:

1. An apparatus for acquiring and projecting a broadband image, the apparatus comprising:
    a probe unit provided, on a probe housing of the probe unit, with a white light source unit configured to emit white light for acquiring a visible light image to a subject, a fluorescence excitation light source unit configured to emit fluorescence excitation light for acquiring an invisible light fluorescence image, an image acquisition unit configured to receive an invisible light fluorescence image signal for the subject, and an image projection unit configured to project an image onto the subject; and
    an image processing unit configured to process an image received from the image acquisition unit,
    wherein the image acquisition unit, the image projection unit, and the white light source unit are arrayed in a central region corresponding to a set first radius from a center of the probe housing of the probe unit, and the fluorescence excitation light source unit is arranged in a surrounding region between the central region and an edge of the probe housing that is positioned in a direction in which a radius increases from the central region.

2. The apparatus of claim 1,
    wherein the white light source unit includes at least one of a light emitting diode, a semiconductor laser, a halogen lamp, and an incandescent lamp, and
    wherein the fluorescence excitation light source unit includes at least one of a light emitting diode, a semiconductor laser, a halogen lamp, and an incandescent lamp.

3. The apparatus of claim 1,
    wherein the fluorescence excitation light source unit comprises a light emitting diode that emits a first band of light, and
    wherein the apparatus further comprises a laser illumination light source unit positioned in the surrounding region of the probe housing, and configured to emit laser light that is within the first band and has a wavelength width less than that of the first band.

4. The apparatus of claim 1,
    wherein the image acquisition unit is configured to receive both the invisible light fluorescence image signal and an image signal of a visible light that is incident from the subject, and
    wherein the image processing unit comprises:
    an image separation unit configured to separate the invisible light fluorescence image signal and the visible light image signal received from the image acquisition unit;
    a color digital camera configured to capture a visible image separated by the image separation unit; and
    an analog camera configured to capture an invisible fluorescence image separated by the image separation unit.

5. The apparatus of claim 4,
    wherein the image processing unit comprises:
    a first display unit configured to display an image captured by the color digital camera;
    a second display unit configured to display an analog fluorescence image captured by the analog camera;
    an analog-to-digital converter configured to convert a signal of the analog fluorescence image captured and transmitted by the analog camera into a digital image signal;
    a third display unit configured to receive the digital image signal from the analog-to-digital converter and display the received digital image signal; and
    a digital image projector configured to receive the digital image signal from the analog-to-digital converter, convert the received digital image signal into a digital image projection signal, and transmit the converted digital image projection signal such that the converted digital image projection signal is projected through the image projection unit.

6. The apparatus of claim 5, further comprising a controller configured to store a signal of a visible light image captured by the color digital camera and the digital image signal generated by the analog-to-digital converter in a database.

* * * * *